United States Patent
Kulprathipanja et al.

(10) Patent No.: US 6,380,428 B1
(45) Date of Patent: *Apr. 30, 2002

(54) METHOD FOR TREATING A LIQUID STREAM CONTAMINATED WITH AN IODINE-CONTAINING COMPOUND USING A CATION-EXCHANGED ZEOLITE

(75) Inventors: Santi Kulprathipanja; John D. Sherman, both of Inverness; Amedeo Napolitano, Des Plaines; John Markovs, Arlington Heights, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/211,791

(22) Filed: Dec. 15, 1998

Related U.S. Application Data

(63) Continuation-in-part of application No. 09/035,798, filed on Mar. 6, 1998, now Pat. No. 5,962,735.

(51) Int. Cl.$^7$ .............................................. C07C 51/47
(52) U.S. Cl. ...................................................... 562/608
(58) Field of Search ......................................... 562/608

(56) References Cited

U.S. PATENT DOCUMENTS

| | | | |
|---|---|---|---|
| 3,634,531 A | 1/1972 | Platz et al. ................... | 260/669 |
| 3,658,467 A | 4/1972 | Maeck ........................... | 23/25 |
| 3,702,886 A | 11/1972 | Argauer et al. .............. | 423/328 |
| 3,769,329 A | 10/1973 | Paulik et al. ................ | 260/488 |
| 4,088,737 A | 5/1978 | Thomas et al. .............. | 423/240 |
| 4,388,231 A | * 6/1983 | Person ........................ | 252/631 |
| 4,554,398 A | * 11/1985 | Barthomeuf et al. ........ | 585/828 |
| 4,615,806 A | 10/1986 | Hilton ......................... | 210/690 |
| 4,735,786 A | 4/1988 | Inoue et al. ................. | 423/240 |
| 4,913,850 A | 4/1990 | Puppe et al. ................ | 252/630 |
| 5,075,084 A | 12/1991 | Wilhelm et al. ............. | 423/241 |
| 5,139,981 A | 8/1992 | Kurland ....................... | 502/11 |
| 5,220,058 A | 6/1993 | Fish et al. ................... | 562/608 |
| 5,227,524 A | 7/1993 | Jones .......................... | 562/608 |
| 5,300,685 A | 4/1994 | Scates et al. ................ | 562/608 |
| 5,344,976 A | 9/1994 | Jones et al. ................. | 562/608 |
| 5,457,230 A | 10/1995 | Yang et al. .................. | 562/608 |
| 5,576,458 A | 11/1996 | Minami et al. .............. | 562/519 |
| 5,801,279 A | 9/1998 | Miura et al. ................. | 562/608 |
| 5,962,735 A | * 10/1999 | Kulprathipanja et al. ... | 562/608 |

FOREIGN PATENT DOCUMENTS

| | | | |
|---|---|---|---|
| RU | | 2104085 | * 12/1995 |

OTHER PUBLICATIONS

Lewis, Hawley's Condensed Chemical Dictionary, twelfth edition, p. 1240, 1993.*

Jolley et al, Iodine . . . FY–83 Report, NTIS Order No.: DE84005464, abstract, Sep. 1983.*

* cited by examiner

*Primary Examiner*—Rosalynd Keys
(74) *Attorney, Agent, or Firm*—John G. Tolomei; Frank S. Molinaro

(57) ABSTRACT

For the removal of trace quantities of iodine-containing contaminants from corrosive liquid feed streams, an adsorbent with distinct advantages over prior-art materials is provided. The treatment method involves the use of a suitable, silica-rich zeolite which has been cation-exchanged with an iodine-reactive metal. This inorganic adsorbent may be used in unbound form, or it can bound with a substantially insoluble porous inorganic refractory metal oxide binder. Reactivation and regeneration techniques, which are generally incompatible with prior-art adsorbent materials, are also disclosed.

13 Claims, No Drawings

METHOD FOR TREATING A LIQUID STREAM CONTAMINATED WITH AN IODINE-CONTAINING COMPOUND USING A CATION-EXCHANGED ZEOLITE

CROSS-REFERENCE TO RELATED APPLICATION

This application is a continuation-in-part of U.S. application Ser. No. 09/035,798 filed on Mar. 6, 1998, now U.S. Pat. No. 5,962,735 B1 which is incorporated by reference.

FIELD OF THE INVENTION

The present invention relates to a novel method for treating a liquid stream contaminated with an iodine-containing compound utilizing a solid adsorbent material. The adsorbent material comprises a zeolite which has been cation exchanged with a metal selected from the group consisting of silver, mercury, copper, lead, thallium, palladium or mixture thereof

BACKGROUND OF THE INVENTION

Methanol carbonylation, the reaction of methanol with carbon monoxide, is used to produce a significant share of the world's acetic acid and represents the basis for virtually all new acetic acid capacity. The fundamental process, whereby methanol and carbon monoxide are reacted in the presence of a rhodium catalyst and methyl iodide promoter, is disclosed in U.S. Pat. No. 3,769,329 and has become well-known as the "Monsanto process". Although numerous improvements have since been developed, the use of an iodine-containing promoter, either as an organic iodide or metal iodide salt, has proven necessary to obtain industrially-competitive reaction rates and production economies.

Unfortunately, the use of any suitable iodine-containing promoter invariably results in the incorporation of trace iodine and organic iodide impurities into the final acetic acid product. These contaminants result from numerous transformations (thermal cracking, recombination, isomerization, etc.) of the iodine-containing catalyst promoters which occur not only in the reactor but also in downstream equipment, such as distillation column reboilers and recycle lines. A resulting array of $C_1$ to $C_{10}$ organic alkyl iodide species is produced, which are removed from the acetic acid product with varying degrees of effectiveness via the standard distillation steps used in downstream purification. Additionally, iodine may be present in the acetic acid product in the form of hydrogen iodide or iodide salts. Ultimately, without supplemental treatment to remove trace iodine-containing contaminants, product acetic acid made using methanol carbonylation technology with even the most careful fractionation steps, will still contain a small amount, typically below 100 parts per billion (ppb) of total iodine (both organic and inorganic) by weight.

The interest in a process for essentially complete removal of iodine-containing contaminants from acetic acid stems from the large share (about 40 to 50%) of its use as a precursor for vinyl acetate monomer (VAM) synthesis. Current methods of VAM production rely on a catalyst which is intolerant to even minute levels of iodine-containing compounds in the acetic acid feedstock. Therefore, the VAM production costs associated with reduced catalyst life increase dramatically with increasing feed iodine concentration.

Several disclosures in the prior art present techniques for the selective removal of iodine-containing species from process streams such as nuclear reactor containment environment off gases as well as emissions from spent nuclear fuel reprocessing operations. For example, U.S. Pat. No. 3,658,467 addresses the removal of radioactive iodine-containing materials from the gaseous waste streams generated either during normal nuclear fuel reprocessing operations or even in the event of a fuel element cladding failure whereby radioactive methyl iodide is formed in significant amounts. The solution proposed in the '467 patent is a zeolite X molecular sieve exchanged with silver for treating the gaseous waste stream. All cited examples referring to the adsorptive ability of this formulation are based on performance in a dry air stream contaminated with trace radioactive methyl iodide. The structures of X-type zeolites are known to have aluminosilicate frameworks with maximum silica to alumina molar ratios, expressed as the ratio of $SiO_2$ to $Al_2O_3$ in the fundamental zeolite framework, of about 3 and pore openings typically in the range of 7 to 8 Å.

In U.S. Pat. No. 4,735,786, an alternate solution for filtering radioactive iodine-containing compounds from nuclear facility exhaust gases in the event of an accident is proposed. In offering an improvement over the prior art, the '786 patent recognizes the practical deficiencies of silver-exchanged zeolite X adsorbent for this service under high humidity conditions. The improvement offered is a different type of adsorbent, characterized as a high silica to alumina molar ratio pentasil zeolite. The adsorbent specified is exemplified by the well-known ZSM-5 type material, which is clearly described in U.S. Pat. No. 3,702,886 as having ten-member rings forming medium-sized pores in the range of 5.1 to 5.6 Å. The teachings and specific examples of the '786 patent are restricted to pentasil zeolites having silica to alumina molar ratios in the range of 15 to 100, preferably 20 to 50.

In U.S. Pat. No. 4,913,850, another solution for methyl iodide removal from gaseous streams is presented, whereby a silver-exchanged "binderless" zeolite material, composed of 80 to 90% zeolite X and 10 to 20% zeolite A, is used. Among the possible candidates for zeolite X materials, those having the faujasite structure are of particular interest. As mentioned previously, zeolite X formulations generally have a maximum silica to alumina molar ratio of 3. In U.S. Pat. No. 5,075,084, the progress of treating radioactive iodine-containing gas streams is continued, where the problem of the proposed silver-exchanged zeolite material catalyzing the highly exothermic reaction of hydrogen and oxygen and, in the extreme case, causing catalytic ignition of hydrogen, is solved. According to the '084 patent, this undesired side reaction is suppressed when a heavy metal such as lead is added to the silver-exchanged adsorbent. The underlying zeolite compositions of the preferred materials in this patent and the previously-mentioned '850 patent are identical.

In U.S. Pat. No. 4,088,737, gaseous radioactive methyl iodide removal is further addressed in a multi-step treatment procedure where the initial gas purification is performed with a silver-exchanged zeolite exemplified by zeolite X. After iodine-compound breakthrough, regeneration and concentration steps are undertaken, which involve i) withdrawing the spent adsorbent from contact with the gaseous waste stream, ii) subjecting the adsorbent to desorption conditions with a hydrogen-rich stream to produce a hydrogen iodide containing off gas, and iii) treating this effluent gas with a lead-exchanged zeolite to readsorb and concentrate the desorbed hydrogen iodide. Lead-exchanged zeolite X is specifically cited as achieving the desired result for the final adsorption step. The advantage of the multi-step treatment is that the long-term storage of the contaminated material is less expensive for the lead-exchanged zeolite, compared to a silver-exchanged material.

In spite of these continuing developments and improvements in trace iodine and organic iodide removal from gaseous effluent streams, the methods employed have been found unsuitable for the more difficult problem of iodine-containing compound adsorption from corrosive liquids, such as commercial acetic acid product streams. Adsorbent carrier materials of the prior art such as zeolite X and zeolite A, which are classified as having low silica to alumina molar framework ratios (typically below 5), have experimentally been proven to be unstable in acetic acid. This means that the dissolution (or leaching) rate of framework components into the liquid is sufficiently large to render such materials ineffective for iodine-containing compound adsorption service in corrosive liquid media.

Depending on the specific silica to alumina framework molar ratio, the pentasil zeolites, exemplified in prior art gas-phase iodine-containing compound removal using ZSM-5, are significantly more stable in acetic acid than zeolite types X and A. However, the pore sizes of pentasil zeolites, as determined by their molecular aluminosilicate crystal channel width, are too small to effectively allow passage of the straight- and branched-chain $C_3$ to $C_8$ alkyl iodides which are generally present as contaminants in commercial acetic acid product streams. In contrast, the iodine-containing compounds present in industrial nuclear power plant waste gases are normally radioactive molecular iodine and methyl iodide only.

Other teachings more specifically apply to iodine-compound removal from corrosive liquid media, where the principal area of concern, as described previously, is in the manufacture of carboxylic acids such as acetic acid via a process which results in a product stream contaminated with trace amounts of iodine-containing byproducts. Thus far, techniques such as adsorptive distillation, iodine scavenger addition, alkyl iodide oxidation to molecular iodine, and others have not achieved practical utility, because such methods not only fail to achieve the extremely low levels of iodine-containing compounds demanded industrially but also require additional purification steps. For this reason, far greater emphasis has been placed on the development of solid materials capable of adsorbing essentially all iodine-containing compounds from acetic acid streams.

For instance, in U.S. Pat. No. 5,457,230, the use of activated carbon fiber is contemplated for this purpose. However, the examples demonstrate the removal of molecular iodine and hydrogen iodide only and fail to specifically disclose the level of iodine-containing compounds in the treated acetic acid stream. In the case of iodine-compound removal from acetic acid, it is the ability of the invention to provide a treated product with only extremely minute levels of total iodine which primarily determines its practical utility. It is known in the art that activated carbon alone can neither remove iodine-containing compounds from commercial acetic acid streams to single parts per billion levels, nor can it effectively remove organic iodide species, such as methyl iodide and hexyl iodide which are commonly present in these product streams, without the use of an iodine-reactive metal.

Recently, considerable development efforts in acetic acid purification technology have focused on resins containing iodine-reactive metals such as silver, mercury, copper, lead, thallium, palladium or combinations of these metals known to react with iodine-containing compounds to form insoluble complexes. For example, in U.S. Pat. No. 4,615,806, the removal of these impurities is achieved with a macroreticulated strong acid cation-exchange resin which is stable in the organic medium and has at least one percent of its active sites converted to the silver or mercury form, presumably by cation-exchange. The use of macroreticulated resins is claimed as an advance over the prior art formulations, which are generally characterized as gel-type ion-exchange resins, for this service. In U.S. Pat. No. 5,139,981, other silver-exchanged resins are offered, along with a novel technique for preparing such resin compositions. In U.S. Pat. No. 5,220,058, a performance benefit is claimed, whereby the subject resin contains thiol functional groups, compared to the prior art sulfonate functional groups, which are exchanged with the iodine-reactive metal. In U.S. Pat. No. 5,227,524, the resin degree of crosslinking is decreased somewhat, resulting in improved silver utilization. In U.S. Pat. No. 5,300,685, the iodine-reactive metal is coordinated, as a salt, with a polymeric resin, rather than being ionically-bound to a cation-exchange resin. In U.S. Pat. No. 5,344,976, a resin guard bed without the iodine-reactive metal is placed upstream of the metal-exchanged resin to scavenge any metal cations in the acetic acid stream which would otherwise potentially displace the iodine-reactive metal. Finally, in U.S. Pat. No. 5,801,279, an improved method of operating the iodine-compound removal step is disclosed in order to reduce the amount of leaching of the iodine-reactive metal into the treated acetic acid effluent stream. As noted in this reference, the dissolution of the iodine-reactive metal is acknowledged as a problem for iodine-compound removal techniques of the prior art whereby metal-exchanged resins are applied.

While the invention of the U.S. Pat. No. 4,615,806 patent and other modified resin-based formulations have been used commercially with some success, resins in general suffer some disadvantages, in addition to the previously-mentioned metal loss, when used in the acetic acid environment of the present invention. More specifically, resins, even those characterized as "stable" are known to "swell" or increase in diameter by as much as 50% when exposed to an organic medium, making bed design difficult. Resins are also vulnerable to decomposition at relatively mild conditions and are furthermore susceptible to chemical attack by corrosive reagents. These factors additionally complicate the use of a resin-based material for the purification of acetic acid.

Also associated with the application of resins in this service is a narrowly-limited range of acceptable operating temperatures due to decomposition, softening, loss of strength, or other detrimental structural changes resulting from thermal effects. Typically, resins begin to chemically decompose at 100 to 200° C., resulting in destruction of their fundamental networks and ion-exchange sites. For example, the preferred resin of the '806 patent is essentially a sulfonated copolymer of styrene and divinylbenzene, and at relatively mild temperatures the acid exchange sites are susceptible to acid-catalyzed desulfonation which leads to release of not only metal cations but also sulfur-containing compounds into the liquid effluent stream. Such materials interfere with further chemical processing of this product. The '806 patent is silent regarding any regeneration or reactivation method because these steps would undoubtedly require temperatures which the macroreticulated resin taught therein cannot withstand without substantial degradation.

As noted in U.S. Pat. No. 5,801,279, operation of the iodine-compound removal step in an acetic acid medium at elevated temperature is beneficial in terms of improving the rate of the desired reaction, which leads to the formation of insoluble metal iodides. However, the resin-based materials traditionally employed for the treatment of acetic acid streams are generally incompatible with high-temperature operation.

The problem therefore addressed by the present invention is to provide an adsorbent for use in removing iodine-containing compounds from commercial acetic acid feed streams where the adsorbent is free of the substantial temperature restrictions, chemical exposure effects, and swelling problems associated with the typical organic materials used in the prior art. There are significant teachings in the prior art associated with the use of non-resin adsorbents that point away from their utility in this treatment service. In particular, in the comparative example recited in U.S. Pat. No. 4,615,806 (column 6, lines 36 to 49), a silver-exchanged zeolite, characterized as $\frac{1}{16}$ inch 5A molecular sieve pellets, was tested in acetic acid for contaminant methyl iodide removal and found to be unstable as evidenced by the continuous silver leaching from the adsorbent and the finding of a yellowish precipitate in the treated effluent. Given this discouraging result, it is remarkable that a suitable inorganic adsorbent for use in this corrosive environment has been discovered.

The adsorbent material in fact comprises a zeolite which has been cation exchanged with a metal known to react with iodine-containing compounds, present in trace amounts in the feed stream of the present invention. This finding of an inorganic material suitable for the treatment of a corrosive acetic acid feed stream is associated with the realization that zeolites with sufficiently high silica to alumina molar ratios are indeed stable in this service. The silica to alumina molar ratio, of course, refers to the composition of the fundamental three dimensional network structure which characterizes the zeolite. It is actually this variable, rather than the type of zeolite itself, which determines its ability to withstand corrosive liquid environments. Experimentally, good results were obtained with silica to alumina molar ratios above about 5, with better results obtained at ratios above about 6.5, and superior results obtained at ratios above about 8. A further unexpected finding was that such a silica-rich zeolite, when used in iodine-containing compound adsorption service of the present invention, can be reactivated using a relatively simple procedure and also regenerated at high temperatures when necessary.

SUMMARY OF THE INVENTION

A primary object of the present invention is to provide a process for treating a liquid feed stream containing an iodine-containing compound comprising contacting the liquid stream with an adsorbent comprising a zeolite which has been cation exchanged with a metal selected from the group consisting of silver, mercury, copper, lead, thallium, palladium, and mixtures thereof, at conditions effective to adsorb the iodine-containing compound on the adsorbent to yield a treated liquid stream.

A secondary object of the present invention is to provide the aforementioned process, further characterized in that the process is carried out until the adsorbent has substantially reached its adsorption capacity, at which point the adsorbent is reactivated by contacting it with a solution of a salt of a reactivation metal where the metal is selected from the group consisting of silver, mercury, copper, lead, thallium, palladium, and mixtures thereof such that an amount of reactivation metal is added to the adsorbent.

Still another object of the present invention is to provide a process for treating a liquid feed stream containing an iodine-containing compound comprising contacting the liquid stream with an adsorbent, further characterized in that the process is carried out until the adsorbent has substantially reached its adsorption capacity, at which point the adsorbent is contacted with a regenerant gas stream comprising hydrogen at conditions effective to strip substantially all of the adsorbed iodine as hydrogen iodide to yield a regenerated adsorbent.

In a specific embodiment the present invention is a process for treating a liquid feed stream containing an iodine-containing compound comprising contacting the liquid stream with an adsorbent comprising silver-exchanged mordenite where the silver is present in an amount of about 1 to about 15 weight percent of the adsorbent.

Other objectives and embodiments are associated with the various preferred procedures and features connected with the invention and are discussed in the following detailed description.

DETAILED DESCRIPTION OF THE INVENTION

The feed for the process of the present invention can be broadly any liquid stream contaminated with one or more iodine-containing compounds. Typically, such feeds are produced in industrial processes which require the use of iodine-containing compounds to promote or catalyze the desired synthesis reaction. Well-documented examples of such reactions include the oxydehydrogenation of various inorganic materials to make the corresponding unsaturated compounds. Of utmost concern to the present invention, however, is the use of organic and inorganic iodine-containing promoters in the catalytic carbonylation of alcohols to yield the corresponding carboxylic acid.

In the specific case of modern methanol carbonylation technology, the iodine-containing promoter is typically methyl iodide, lithium iodide, hydrogen iodide, or, more likely, some combination of these components. The acetic acid produced, however, will normally contain a broader range of iodine-containing compounds, including traces of $C_1$–$C_{10}$ linear and branched organic iodides as well as inorganic iodide salts of lithium and other cations either used to catalyze the reaction, formed from corrosion of the plant metallurgy, or introduced in downstream purification operations. This large variety of possible iodine-containing compounds results from the "scrambling" or recombination and rearrangement reactions of iodine-containing compounds, initially introduced as promoters, in recycle lines and processing equipment.

Normally, however, multiple distillation steps downstream of the reactor are used to separate the desired acetic acid product from unconverted reactants, catalyst promoters, and byproducts from both equilibrium and irreversible reactions. As a result of these purification measures, the predominant alkyl iodide species contaminating the acetic acid product, and thus the feed stream to the present invention, are $C_1$ to $C_8$ alkyl iodides. Also included in this feed stream are a small amount of water, generally limited to about 2000 parts per million (ppm) by weight, and trace amounts of byproduct aldehydes, alkanes, ketones, and carboxylic acids heavier than acetic acid which together normally account for less than about 100 ppm by weight of the total acetic acid stream. These other impurities do not significantly affect the ability of the adsorbent of the present invention to remove the iodine-containing compounds. In addition to the fractionation operations themselves, the injection of methanol into the first distillation column after the carbonylation reactor is commonly employed, as taught in U.S. Pat. No. 5,576,458, to further reduce the total iodine content of the acetic acid. This is achieved through the conversion of trace hydrogen iodide to methyl iodide, which is more easily separated from acetic acid by subsequent distillation steps. Using this technique combined with fractionation, typical modern industrial methanol carbonylation plants can produce acetic acid with less than about 100 ppb by weight of total iodine contamination.

Prior to contacting the iodine-compound contaminated acetic acid feed stream with the adsorbent of the present invention, pretreatment steps of the prior art other than methanol injection and fractionation may be suitable to improve the effectiveness of trace iodine-compound removal by adsorption. For example, a an optional pretreatment that is within the scope of the present invention is described in U.S. Pat. No. 4,615,806 where a carbonaceous material is used specifically to remove hydrogen iodide and molecular iodine prior to the iodine-containing compound adsorption treatment. Particularly effective in this service are carbonaceous materials including activated carbons, wood charcoal, bone char, lignite, and others which may be impregnated with alkali metals known to increase the inorganic iodine compound chemisorption capacity.

Another pretreatment option, as mentioned previously, is disclosed in U.S. Pat. No. 5,344,976, whereby a cation exchange resin guard bed without any iodine-reactive metal is placed upstream of the iodine-containing compound removal adsorbent of the present invention to scavenge any metal cations, thus preventing their exposure to the adsorbent. As is well known to commercial producers of acetic acid, metal cation contamination of the product can stem from reaction catalysts and co-catalysts, corrosion of the plant metallurgy, or downstream processing operations such as neutralizing caustic injection. To effectively remove undesired cations which could otherwise potentially displace the iodine-reactive metal of the adsorbent of the present invention, a number of strong acid cation exchange resins are suitable, when used in their hydrogen form. Such resins include Amberlyst 15 (available from Rohm and Haas Company, Philadelphia, Pa.) and others, as described in the '976 patent. Depending on the specific characteristics of the acetic acid feed stream, the use of either a guard bed of carbonaceous material, cation exchange resin, or both may prove beneficial for extending the practical life of the adsorbent of the present invention.

In the present invention, the novel adsorbent used to treat the iodine-compound contaminated feed comprises a zeolite which has been cation exchanged with a metal that is reactive with iodine and iodine-containing compounds. The adsorbent is typically in a pellet, pill, or extrudate form. Furthermore, the distinguishing and novel characteristics of the zeolite are its silica to alumina framework ratio and pore size, both of which are particularly important to the overall effectiveness of the material for use in treating corrosive feed streams. As explained previously, the silica to alumina molar ratio of the zeolite must allow for sufficient stability in corrosive environments. A simple test to determine whether the silica content of the zeolite is sufficient comprises subjecting it to a solution of pure acetic acid at a temperature corresponding to the proposed operating temperature, preferably from about 30° C. to about 150° C., for 24 hours. Any substantial dissolution of the framework alumina appears as a cloudy precipitate in the liquid. Another practical consideration for determining the optimal silica to alumina molar ratio of the zeolite is that the amount of available exchange sites for loading the iodine-compound reactive metal directionally decreases with increasing silica content. Therefore, zeolites with excessive silica to alumina molar ratios (greater than about 15) are not recommended. It is important at this point to distinguish the silica to alumina ratio (or $SiO_2/Al_2O_3$ ratio) from another commonly-used term in the art, the "Si/Al ratio", which is exactly half of the silica to alumina molar ratio.

For adsorption activity, three broad zeolite classifications exist and are described as having either 8-, 10-, or 12-member rings according to the number of tetrahedral molecule building blocks linked together in the zeolite structure. In the present invention, the preferred zeolites are those of large-pore consideration, whose molecular sieve channels are formed by 12-member rings. Such large-pore zeolites, with channel aperture widths of greater than about 6 Å, allow for fast diffusion of even the high molecular weight and branched alkyl iodide compounds, known to contaminate the liquid feed, to the iodine-reactive metal-exchanged sites. Useful zeolites within the 12-member ring classification are mordenite, zeolite Y, zeolite L, omega, ZSM-12 and beta. The type Y zeolites in this case are broadly defined and described according to synthesis procedures and structural details in U.S. Pat. No. 3,130,007 which is incorporated by reference. Zeolites L, omega, ZSM-12, and beta are defined and described according to synthesis procedures and unique structural details in U.S. Pat. No. 3,216,789, U.S. Pat. No. 4,241,036, U.S. Pat. No. 3,832,449, and U.S. Pat. No. 3,308,069, respectively, all of which are incorporated by reference. Useful zeolites within the 10-member ring classification are ZSM-5, defined in U.S. Pat. No. 3,702,886, incorporated by reference; ZSM-11, defined in U.S. Pat. No. 3,709,979, incorporated by reference; ZSM-23, defined in U.S. Pat. No. 4,076,842, incorporated by reference; some of the silicalite materials, defined in U.S. Pat. No. 4,061,724, incorporated by reference; and ferrierite.

Mordenite is a naturally-occurring siliceous zeolite which is available as either an 8-member or 12-member ring structure. It is the 12-member ring structure, known as "large port" mordenite or "zeolon", which is most applicable to the present invention. The structure, composition, properties, and method of synthesis of mordenite zeolite are described in *Zeolite Molecular Sieves* by Donald W. Breck (John Wiley and Sons, 1974) at pages 122 to 124 and 162 to 163 which may be consulted for further details.

Zeolites having the Y structure, modified to achieve a specific range of silica to alumina framework ratios, are also of primary interest to the present invention. In this case the silica to alumina molar ratio is preferably between about 5 and about 15, most preferably between about 8 and about 12. Particularly preferred are Y zeolites modified either by steam stabilization, chemical treatment, or a combination of these procedures. Steam stabilization of a Y zeolite normally involves calcination of its ammonia or hydrogen form starting material at relatively high temperatures (above about 500° C.) in the presence of steam. Typically, this procedure is followed by additional ammonia ion-exchange procedures and subsequent steam calcination treatments until the sodium content of the resulting zeolite is below 0.5% by weight, calculated as sodium oxide. U.S. Pat. No. 3,929,672, which is incorporated by reference, contains additional details concerning a preferred steam-stabilized Y zeolite useful in the present invention.

Another type of modified Y zeolite of interest in this case is the LZ-210 version which requires chemical treatment to increase its silica to alumina framework ratio through "secondary synthesis" technology. A definition of zeolite LZ-210 and details of its synthesis from conventional Y zeolite by chemical treatment is given in U.S. Pat. No. 4,503,023, which is incorporated by reference. The last type of modified Y zeolite particularly useful in the present invention is characterized as Y-85, which is a steam-stabilized and chemically-modified zeolite Y. Preparation details for Y-85 are fully disclosed in U.S. Pat. No. 5,013,699, which is incorporated by reference. Experimentally, however, of the Y zeolites, it has been found that the best practice is to use LZ-210 type materials that have molar silica to alumina framework ratios preferably from about 5 to about 15, most preferably between about 8 and about 12. LZ-210 zeolite is thus a particular type of hydrophobic, large-pore, zeolitic material that is suitable for use in the present invention.

The zeolitic molecular sieve used in the present invention is activated by suitable ion exchange with any metal known to be reactive with iodine-containing compounds. Particularly, ion exchange with silver, mercury, copper, lead, thallium, palladium or mixtures thereof gives good results for use in liquid-phase iodine compound adsorption service. It is well known that, for converting the sodium, ammonia, or hydrogen form of the molecular sieve starting material into the metal-exchanged form suitable for use in the present invention, any water soluble salt of the metals recited above is appropriate as an ion-exchange medium. Also, a non-aqueous organic medium may be used provided sufficient solubility of the salt is possible. Acetate, nitrate, or halide salts are ordinarily used for the ion-exchange procedure and the appropriate conditions are typically room temperature and atmospheric pressure. The contact of cation-rich solutions with the zeolite-containing molecular sieve can be repeated to obtain a desired metal loading. In some cases, drying and calcining the material between ion-exchange treatments may improve penetration of the metal into the zeolite molecular sieve material. After completion of the ion-exchange step, it is necessary to dry the ion-exchanged material at about 100° C. to about 200° C. for several hours to remove any residual solution and activate the zeolite.

For the application of the present invention, the most preferred metal for ion exchange is silver, with best results achieved when the silver loaded represents about 1% to about 15%, preferably about 8% to about 14% on an elemental basis, of the dried adsorbent weight. Where the zeolite is available only in a powder form, it is often desired to bind this fine material into larger particles such as pellets, extrudates, or spheres. For such cases, the ion-exchange procedure can be applied directly to the zeolite powder prior to binding. Alternatively, the preferred procedure is incorporation of the metallic cation into the zeolite after binding it into a particle suitable for a commercial packed-bed system. Typically, the crystal size of molecular sieve powder is 0.1 to 6 microns but the crystallites are agglomerated into particles of 10 to 20 microns in diameter. In contrast, particles useful for fixed-bed applications have diameters of about 1600 microns, although their exact size is not critical, provided the bed pressure drop is acceptable in commercial operation. It is to be noted that mordenite zeolite powder alone may be formed into various shapes large enough so that, for the practical purposes of the present invention, a separate binding agent may not be necessary.

In the prior art, there are many ways described for combining a binder material with molecular sieves to make larger size particles with sufficient strength suitable for the present invention. It is of course, necessary that the binder material is not soluble to any significant degree in the corrosive liquid feed stream to be treated. The test for the appropriate degree of insolubility is a finding of below about 10 ppm of the binder material in the treated effluent stream of the present invention under iodine-compound adsorption conditions after 100 hours. The initial 100 hours provides a reasonable period for the adsorbent to stabilize and reach its start-of-run composition. Binder materials found to satisfy the substantial insolubility requirement and exhibit utility in preparing the adsorbent of the present invention are the inorganic refractory metal oxides selected from the group consisting of silica, titania, zirconia, chromia, boria, vanadia, magnesia, and mixtures thereof Preferred binder materials are selected from the group consisting of silica, titania, zirconia, and mixtures thereof Silica, in addition to its stability in corrosive media, is most preferred in practice because of its ready availability and low cost. Binder materials such as alumina which are susceptible to attack in acidic solutions are not suitable.

If it is determined that shaped agglomerates of the zeolitic molecular sieve and binder material are to be formed, an extrusion procedure is incorporated where the zeolite and binder are first blended in the proper ratio. The resulting mixture is combined with water and a peptizing agent to form a gel or dough which is then extruded into pellets most commonly having a circular cross section. The union of the binder and zeolite material can also result in the formation of spherical beads, using technology well-known in the adsorbent art. It is certainly possible to form other cross sectional shapes; the main objective is to reduce the gross diffusional path of iodine-containing contaminants into the adsorbent pores.

If spherical adsorbent agglomerates are desired, the preferred method of forming is according to the well-known "oil-dropping" technique. This procedure essentially involves the initial synthesis of an appropriate sol, or carrier material, of the binder used for suspending the active zeolitic material. Details of this technique are provided in U.S. Pat. No. 2,620,314, which is incorporated by reference. In the case of the preferred binders mentioned for producing the adsorbent material of the present invention, it is appropriate to make an acidic hydrosol that can be gelled using the type of temperature-activated gelling agent set forth in the '314 patent. The preferred temperature-activated gelling agent is hexamethylenetetramine (HMT). It is also recognized that in some cases silica sols may gel without a gelling agent or even a substantial change in temperature. This type of sphere formation is also within the scope of the present invention. Types of silica sols used to form the silica binder are commercially available as aquasols or organosols containing dispersed colloidal silica particles.

For performing oil dropping with a silica sol, an inverted silica sol, produced by an acid addition technique and a basic gelling agent such as a mixture of urea and HMT, is preferred. When a zirconia binder is used for the adsorbent preparation, the preferred acidic sol is an aqueous zirconyl hydroxylchloride and urea solution. When a titania binder is used, the acidic sol is preferably a solution of titanyl oxychloride and urea.

The important feature of the technique for forming agglomerates is to avoid any significant binder blockage of molecular sieve pores by the sol. In the case of the present invention, this phenomenon, called "binder blinding", would cause binder interference with access of the iodine-containing compounds to the active sites in the molecular sieve. To overcome this effect, it may be necessary to add an inert diluent, typically of somewhat smaller size than the zeolite powder, to the mixture of zeolite and binder prior to agglomerate formation. This diluent can act as a bridging material for the binder and molecular sieve, thus preserving the zeolite pore system. Typical inert diluents used to prevent binder blinding are non-colloidal silica and some types of clays resistant to low pH conditions. An essential feature of the present invention, of course, is that the chemical characteristics of the binder are properly matched with those of the zeolite, if such a bound zeolitic material is in fact used. Regardless of the method of agglomerate formation, the resulting particles should be dried at about 80° C. to about 150° C. for several hours and then calcined in dry air.

Typically, the initial forming stage in the production of extrudates, beads, pellets, or other shapes yields "green" particles which posses sufficient strength for a subsequent calcination step to set the binder and activate the molecular sieve. The temperatures most commonly used for this calcination or firing step range from about 450° C. to about 700° C., preferably about 600° C. to about 650° C. The binder is typically present in the in an amount of less than about 30% by weight, preferably between about 15% and about 25% by weight of the binder and zeolite combined. Therefore, where a bound cation-exchanged zeolite is used for the adsorbent of the present invention, the zeolite should comprise at least about 70%, and preferably from about 75% to about 85% of the adsorbent weight, not considering the weight of the cation-exchange metal ("metal-free" basis).

According to the present invention, the liquid feed stream contaminated with iodine-containing compounds is contacted with an adsorbent comprising a zeolite exchanged with metallic cations, which are reactive with the iodine-containing impurities. A binder material may or may not be necessary, depending on the type of zeolite used. Of the zeolite materials mentioned previously which are most preferred for the adsorbent of the present invention, mordenite does not necessarily require the use of a porous refractory inorganic oxide binder.

The adsorption conditions applicable to the present invention include an absolute pressure at least sufficient to maintain the feed stream as a liquid. In most cases, this absolute operating pressure is about 0.5 to about 10 atmospheres (about 51 to about 1010 kPa), preferably about 1 to about 5 atmospheres (about 101 to about 505 kPa) at a temperature of about 20° C. to about 350° C., preferably about 30° C. to about 150° C. In general, higher temperatures improve the interaction of the iodine-containing contaminants with the reactive metal which is deposited onto the adsorbent and thereby increase the utilization of the reactive metal sites. It is also noted that the adsorbent of the present invention can successfully withstand considerably higher temperatures than the resin-based adsorbent formulations of the prior art. A suitable liquid hourly space velocity (LHSV) is in the range from about 0.5 to about 15 $hr^{-1}$, preferably about 1 to about 10 $hr^{-1}$. As understood in the art, the LHSV is the hourly volumetric liquid feed flow rate divided by the adsorbent volume and represents the reciprocal of the average time of the liquid within the adsorbent bed.

After an extended period of operation in iodine-compound removal service the reactive metal is gradually converted to its metal iodide, while the zeolite ion-exchange sites are concurrently changed to their hydrogen form. Electron microscopy analysis of silver-loaded zeolitic adsorbents after use has indicated a migration of silver iodide molecules and subsequent agglomeration at various points on the outer surface of the adsorbent. As substantially all of the iodine-reactive metal is converted to metal iodide, the adsorbent gradually loses its effectiveness, so that the treated liquid stream may no longer conform to the product quality specifications demanded in terms of total iodine content. At this point, the adsorbent has substantially reached is adsorption capacity and a simple metal exchange procedure can restore activity.

The technique requires subjecting the adsorbent, either in situ or ex situ, to a solution of iodine-reactive metal cations, preferably the same type of solution used originally for the cation-exchange procedure. The ion-exchange treatment introduces an additional portion of the active metal, thereby re-establishing the metal-exchanged zeolite sites active for iodine-containing compound adsorption. Thus, the adsorbent activity for iodine-compound removal is restored. The amount of metal added in this reactivation treatment is preferably about 0.5 to about 1.5 of the amount originally deposited onto the carrier, with the specific quantity determined by the extent of deactivation of the adsorbent activity. The reactivation procedure can be repeated multiple times to vastly extend the adsorbent life, until the active zeolite metal-exchange sites become obstructed with silver iodide to such an extent that more severe treatment steps are necessary to restore the iodine-containing compound adsorption capacity.

When the reactivation procedure fails to reestablish sufficient iodide removal capacity of the spent adsorbent, it is possible to free the molecular sieve pores of the iodine-containing compounds adsorbed during iodide removal service. A beneficial regeneration step involves exposure of the spent adsorbent to a high-temperature hydrogen-containing gas stream. Of course, as is common in industrial hydrogen streams, the gas used in the regeneration step may comprise a mixture of hydrogen and a diluent gas selected from the group consisting of nitrogen, argon, methane, ethane, propane, and mixtures thereof This treatment has proven to reduce silver to its elemental form and simultaneously liberate hydrogen iodide. As is explained in U.S. Pat. No. 4,088.737, this regeneration procedure requires a moderate absolute pressure of about 1 to about 10 atmospheres (about 101 to about 1010 kPa), a high temperature of about 400° C. to about 550° C., and a gas hourly space velocity (GHSV) of about 400 to about 1000 $hr^{-1}$. This treatment generates a gas stream containing hydrogen iodide which can be either neutralized or re-adsorbed onto a cheaper adsorbent for long-term storage.

Once the iodine is stripped from the adsorbent using this technique, the metallic reagent remaining in the adsorbent can be oxidized to its cationic form, which is effective for the application of the present invention. The procedure to oxidize the iodine-compound reactive metallic ingredient and to re-exchange the resulting cations with the active sites of the zeolite portion of the adsorbent are well known in the art. An oxygen-containing gas stream is often used for the oxidation procedure, and air is typically chosen for convenience. However, other oxidizing agents, such as oxygen, carbon monoxide, nitrogen oxide, and mixtures thereof are also acceptable even if they contain some impurities.

Within the scope of the present invention, it is possible to pass the treated liquid effluent, which has been depleted in iodine-containing compounds to less than 10 and preferably less than 5 ppb (measured as total elemental iodine) by weight, over a second bed of the adsorbent, in which the zeolite component has not been cation-exchanged with an iodine-reactive metal. This serves to recover or "trap" any metallic cations originally present in the first bed of the metal-exchanged zeolite-containing adsorbent which were released into the treated liquid due to displacement by hydrogen ions or metallic cation contaminants in the liquid feed stream during the adsorption step. This procedure would therefore ensure that cations released from the adsorbent during the treatment method of the present invention are retained within the system and therefore do not contaminate the effluent liquid.

It is, of course, also within the scope of the present invention to periodically reverse the flow through the aforementioned two bed system to drive an active mass-transfer zone of metallic iodine-reactive cations from one bed to the other, thereby making them continually available for adsorption of the iodine-containing compounds in the liquid feed. Details associated with the operation of such a two bed system are well known to those skilled in the art. To scavenge any cations, including those used for adsorption of iodine-containing compounds, exiting with the liquid effluent of the treatment step of the present invention, it is also possible to use any suitable commercial product selective for the adsorption of cations. Especially preferred for this service are cation exchange resins such as Amberlyst 15 in the hydrogen form.

The adsorption step can be performed using a fixed-, moving-, or fluidized-bed system or a batch operation. It is preferred to employ a fixed-bed system with the iodine-containing compound contaminated liquid feed stream continually flowing through the adsorption zone of active adsorbent. Of course, the adsorption step may use a plurality of adsorption zones with the desired conditions maintained between and within the separate beds. In any case, depending on iodine-compound concentration in the liquid feed stream, the operating conditions of the adsorption step can be manipulated to achieve an effluent liquid stream containing less than about 10 ppb by weight of total iodine, calculated on an elemental basis, and preferably less than about 5 ppb by weight. Regarding the mechanics of the operation, it is possible to use swing-bed systems of the prior art to alternate beds of adsorbent between the adsorption, reactivation, and regeneration steps of the present invention.

The following examples illustrate the benefits and advantages associated with the present invention and contrast it with the prior art, particularly in the case where the use of zeolite-containing adsorbents of the type of the present invention was attempted but did not yield satisfactory results. While these examples are provided to illustrate the present invention they are not intended to limit it.

COMPARATIVE EXAMPLE 1

The Comparative Example III of U.S. Pat. No. 4,615,806 (column 6, lines 35 to 49), is incorporated for reference. According to this comparative example, an attempt was made to remove methyl iodide from an essentially pure acetic acid stream utilizing 50 ml of 1/16 inch (1.6 mm) particle size 5A molecular sieve pellets. This non-resin carrier material contained unspecified amounts of zeolite A which had been ion-exchanged with silver from a silver nitrate solution. A synthetic solution of 0.865% methyl iodide in acetic acid was then passed over this bed of silver-exchanged 5A molecular sieve particles at apparently ambient temperature and pressure at an LHSV of 1 hr$^{-1}$. Continuous leaching of silver was noted, along with the formation of a yellowish precipitate in the treated acetic acid effluent, which was believed to be silver iodide. These results would imply that breakthrough of the methyl iodide occurred very quickly and therefore that performance was unacceptable.

COMPARATIVE EXAMPLE 2

An adsorbent comprising zeolite X (defined in U.S. Pat. No. 2,882,244) in a powder size of 0.1 to 6 microns was bound with a kaolin-type clay to make agglomerates ranging in diameter from 150 to 840 microns. The amount of zeolite X used in this preparation resulted in uncalcined agglomerates having 80% zeolite by weight. These agglomerates were then dried at 75° C. for 3 hours and calcined in dry air at a final temperature of 600° C. for 4 hours. The calcined adsorbent particles were soaked in an aqueous solution of silver nitrate until sufficient silver had been cation exchanged with zeolite X to result in particles containing 10.5% silver by weight in the form of exchanged silver cation. The silver-exchanged particles were water washed to remove residual exchange solution and then dried at 300° C. for 2 hours. The final resulting adsorbent had a silica to alumina framework molar ratio of 2.5, a silver content of 10.5% by weight and an ABD (apparent bulk density) of about 0.7 grams per milliliter.

A breakthrough test was then performed to determine the capacity of this adsorbent containing silver-exchanged zeolite X for adsorption of methyl iodide from an acetic acid solution. A feed solution containing about 500 ppm methyl iodide in acetic acid was passed through a 50 ml packed bed containing these adsorbent particles. The iodine-containing compound adsorption conditions included an LHSV of 4 hr$^{-1}$, an absolute pressure of 6.8 atmospheres, and a temperature of 60° C.

Almost immediately, the effluent from the test zone turned cloudy and a precipitate formed. Upon analysis the precipitate was found to contain silver iodide, indicating that iodide breakthrough occurred very early in the run. In addition, the effluent showed a substantial content of alumina, a symptom of zeolite framework breakdown as well as binder degradation and leaching. Performance was unacceptable.

EXAMPLE 1

An adsorbent was prepared using large-port mordenite zeolite (described in *Zeolite Molecular Sieves* by Donald W. Breck, p. 163) having a silica to alumina framework molar ratio of about 11 in unbound form. Particle sizes of the mordenite ranged from 0.1 to 6 microns. The zeolite was silver-exchanged, water washed, and dried in the manner described in Comparative Example 2. The resulting silver-exchanged mordenite had 19.1% silver by weight and an ABD of 0.65 grams per milliliter. The silver content was determined using atomic adsorption Spectroscopy (AAS) analysis.

A 15 ml adsorbent sample was loaded into a 10 mm i.d. vessel and contacted with a feed stream comprising acetic acid contaminated initially with 139.5 ppm by weight of methyl iodide. The operating conditions were 60° C., 4 hr$^{-1}$ LHSV, and atmospheric pressure. In order to accelerate the breakthrough of methyl iodide and thereby allow for a determination of adsorptive capacity within a reasonable time frame, the feed methyl iodide concentration was increased stepwise near the end of the experiment to 678.6 ppm by weight. The liquid effluent stream was periodically analyzed for organic iodide using gas chromatography (GC) equipped with an Electron Capture Detector (ECD). Results showed that the total iodine level in the treated liquid stream was below the 1 weight ppb detection limit of the analyzer capability for the first 300 ml of effluent. The calculated iodine-compound removal capacity of this adsorbent, based on these results, was 10.15 mg iodine per milliliter of adsorbent.

EXAMPLE 2

An adsorbent was prepared using a special type of zeolite Y known as zeolite LZ-210 (defined in U.S. Pat. No.

4,503,023) having a silica to alumina framework molar ratio of 10 and an alumina binder, according to the extrusion method previously described. The resulting extrudate particles were then ground and particles of 150 to 840 microns in diameter were separated and retained. Analysis showed that the material was 80% zeolite and 20% binder by weight. The resulting material was dried, calcined, silver-exchanged, water washed, and dried again in the same manner as in Comparative Example 2. The resulting silver-exchanged, alumina-bound, and zeolite Y-containing adsorbent had 13.2% silver by weight, a zeolite silica to alumina framework molar ratio of 10, and an ABD of 0.71 grams per milliliter.

A breakthrough test was performed using the same feed and conditions as specified in Comparative Example 2. However, the sample size was reduced from 50 to 9 ml. The run was continued for 22.2 hours with the total iodine concentration of the effluent stream below 5 ppb by weight, again measured using GC-ECD. At that time, methyl iodide breakthrough occurred, based on the effluent solution analysis, which showed greater than 10 ppb by weight of total iodine. From the amount of iodine adsorbed before breakthrough, the calculated iodine-compound adsorption capacity was 45.6 mg iodine per milliliter of adsorbent.

Despite the apparent success of this experiment, the effluent solution was cloudy and, based on analysis, found significantly contaminated with alumina due to binder leeching. Therefore, alumina is not a preferred binder for long-term commercial service, although it may be acceptable for short-term operation.

EXAMPLE 3

Example 2 was repeated except that zirconia was substituted for alumina as the zeolite LZ-210 binder. The zirconia accounted for 20% of the adsorbent weight, on a silver-free basis. Breakthrough occurred, as defined in Example 2, at an adsorbent capacity of 44.9 mg of iodine per milliliter of adsorbent. Analysis of the effluent in this case, however, showed no significant amounts of zirconia and only trace amounts of silica and alumina, indicating that zirconia is a preferred binder for long-term commercial service.

EXAMPLE 4

Example 2 was repeated except that the LZ-210 zeolite having a silica to alumina framework molar ratio of 6.5 and a silica binder were used in the adsorbent preparation. The silica binder accounted for 20% of the adsorbent weight, on a silver-free basis. Also, the adsorbent contained about 9% silver by weight and had an ABD of about 0.6 grams per milliliter.

Breakthrough occurred, as defined in Example 2, at 36 mg of iodine per milliliter of adsorbent. During the first 3 hours on stream, a white precipitate was observed in the effluent. Analysis showed this precipitate to be alumina, indicating that an increase in the zeolite silica to alumina framework molar ratio was occurring in situ. This finding demonstrates that a more silica-rich zeolite would be preferable, due to its enhanced stability, as the primary component of the adsorbent.

EXAMPLE 5

Example 2 was repeated except that titania was substituted for alumina as the LZ-210 zeolite binder. The titania accounted for 20% of the adsorbent weight, on a silver-free basis. Also, the adsorbent contained 7.7% silver by weight and had an ABD of about 0.6 grams per milliliter.

The breakthrough test results showed a capacity for iodine adsorption of 21 mg per milliliter of adsorbent.

EXAMPLE 5A

A second sample of the fresh adsorbent from Example 5 was subjected to a further silver-exchange using the same ion-exchange and finishing procedures as those described for preparing the fresh adsorbent. Analysis of the adsorbent after undergoing this additional metal exchange showed it contained 10.1% silver by weight.

The breakthrough test, as described in Example 2, was then repeated using the same feed and adsorption conditions as in Example 5. It was found that the twice-exchanged adsorbent had a capacity of 23 mg of iodine per milliliter of adsorbent before iodine breakthrough reached 10 ppb concentration in the effluent liquid. Thus, the iodine-compound adsorption capacity was improved by about 10%.

EXAMPLE 5B

A sample of the fresh adsorbent from Example 5A was subjected to yet another silver-exchange as outlined before. Analysis of the adsorbent after this third silver-exchange procedure showed it contained 11% silver by weight.

The breakthrough test of Example 2 was repeated and the calculated adsorbent capacity was 26 mg of iodine per milliliter of adsorbent. This represented a further improvement of 13% over the fresh adsorbent performance noted in Example 5A and demonstrated the beneficial effects of multiple ion-exchange procedures in the adsorbent preparation.

EXAMPLE 6

Example 5 was repeated except that the binder was zirconia and the method of preparation was according to the oil-dropping procedure described previously. The relative amounts of zeolite and binder were maintained such that they represented 80% and 20% by weight, respectively, of the finished adsorbent on a silver-free basis. The silver content of the fresh adsorbent was 11.4% by weight, based on AAS analysis. The breakthrough test results for the fresh adsorbent as well as for 5 reactivation cycles of the spent adsorbents after undergoing re-silver exchange procedures at the end of each cycle, as specified in Example 5A, are provided in Table 1.

TABLE 1

RESULTS OF SIX CYCLES OF USE OF SILVER-EXCHANGED LZ-210 & ZIRCONIA BINDER

| Cycle No. | Silver Content in wt. % | Breakthrough Test Capacity in mg/cc of adsorbent |
| --- | --- | --- |
| 1 | 11.4 | 19.1 |
| 2 | NA | 21.3 |
| 3 | NA | 25.2 |
| 4 | NA | 27.9 |
| 5 | NA | 21.7 |
| 6 | NA | 21.7 |

From the results in Table 1, the spent adsorbent can be reactivated by the re-silver exchange procedure at least 5 times without significant loss of adsorbent capacity for iodine-containing compounds.

EXAMPLE 7

Example 4 was repeated except that the LZ-210 zeolite used for the adsorbent preparation had a silica to alumina framework molar ratio of 10. Also, the silica binding was performed using the previously-described oil-dropping procedure.

The breakthrough test results, showing the adsorbent capacity for iodine as defined in Example 2, for three samples of fresh adsorbent are given in Table 2.

TABLE 2

RESULTS OF THREE SAMPLES OF FRESH ADSORBENTS OF SILVER-EXCHANGED LZ-210 WITH SILICA BINDER

| Sample No. | Silver Content in wt. % | Breakthrough Test Results in mg/cc of Adsorbent |
|---|---|---|
| 1 | 10.2 | 18.2 |
| 2 | 10.2 | 19.5 |
| 3 | 10.2 | 20.5 |

These results indicate good reproducibility of the silica-bound adsorbent preparation procedure and performance.

EXAMPLE 8

Example 4 was repeated with an LZ-210 zeolite having a silica to alumina framework molar ratio of 10 and with the feed solution in the breakthrough test containing hexyl iodide substituted for methyl iodide in an average concentration of about 10 ppm of total iodine by weight.

The results of the breakthrough test showed a capacity of the adsorbent using this heavier organic iodide compound of 15 mg of iodine per milliliter of adsorbent without any degradation of the zeolite or binder. Breakthrough did not occur until after 36 days on stream.

EXAMPLE 9

The spent adsorbent of Example 6, having undergone 6 cycles of testing and reactivation, can be subjected to the regeneration procedure of the present invention. After water-washing to remove any loosely-bound organic material, the spent adsorbent can be dried at 300° C. for 2 hours. The dried adsorbent can then be contacted with a dry gaseous mixture of 50% $H_2$ and 50% $N_2$ by volume at a GHSV of 500 $hr^{-1}$, an absolute pressure of 3 atmospheres, and a temperature of 525° C. for a period of about 20 hours until the gaseous effluent is found free of hydrogen iodide.

The resulting iodine-stripped adsorbent can then be subjected to a mild oxidation treatment to facilitate oxidation of the elemental silver generated in the hydrogen iodide stripping step.

The breakthrough test used in Example 5 can then be repeated with this regenerated adsorbent and reasonable results are expected.

What is claimed is:

1. A process for treating a liquid feed stream containing an iodine-containing compound comprising contacting the liquid feed stream with an adsorbent comprising a zeolite having a silica to alumina molar ratio from about 5 to about 15 which has been cation exchnaged with a metal selected from the group consisting of silver, mercury, copper, lead, thallium, palladium, and mixtures thereof; at conditions effective to absorb the iodine-containing compound on the adsorbent to yield a treated liquid stream.

2. The process of claim 1 where the zeolite is mordenite.

3. The process of claim 1 where the adsorbent further contains an inorganic refractory metal oxide binder.

4. The process of claim 3 where the binder is selected from the group consisting of silica, titania, zirconia, chromia, boria, vanadia, magnesia, and mixtures thereof.

5. The process of claim 1 where the metal is silver and is present, on an elemental basis, in an amount from about 1 to about 15 weight percent of the adsorbent.

6. The process of claim 1 where the iodine-containing compound is an alkyl iodide having from 1 to 8 carbon atoms.

7. The process of claim 1 where the adsorption conditions include a temperature from about 30° C. to about 150° C., pressure from about 1 to about 5 atmospheres, and a liquid hourly space velocity from about 0.1 to about 10 $hr^{-1}$.

8. The process of claim 1 where the treated acidic organic liquid stream contains less than about 10 parts per billion of total iodine by weight.

9. The process of claim 1 where the acidic organic liquid feed stream comprises an acetic acid feed stream.

10. The process of claim 1 further characterized in that the process is carried out until the adsorbent has substantially reached its adsorption capacity, at which point the adsorbent is reactivated by contacting it with a solution of a salt of a reactivation metal where the metal is selected from the group consisting of silver, mercury, copper, lead, thallium, palladium, and mixtures thereof such that an amount of reactivation metal is added to the adsorbent.

11. The process of claim 1 further characterized in that the process is carried out until the adsorbent has substantially reached its adsorption capacity, at which point the adsorbent is regenerated in a regeneration process comprising:

1) contacting the adsorbent with a regenerant gas stream comprising hydrogen at conditions effective to strip substantially all of the adsorbed iodine-containing compound as hydrogen iodide to yield a regenerated adsorbent, and 2) treating the regenerated adsorbent with an oxidizing agent such that the metal is oxidized.

12. The process of claim 11 where the regenerant gas stream comprises hydrogen and a diluent gas selected from the group consisting of nitrogen, argon, methane, ethane, propane, and mixtures thereof.

13. The process of claim 11 where the oxidizing agent is selected from the group consisting of oxygen, air, carbon monoxide, nitrogen oxide, and mixtures thereof.

* * * * *

UNITED STATES PATENT AND TRADEMARK OFFICE
CERTIFICATE OF CORRECTION

PATENT NO. : 6,380,428 B1  
DATED : April 30, 2002  
INVENTOR(S) : Kulprathipanja et al.

It is certified that error appears in the above-identified patent and that said Letters Patent is hereby corrected as shown below:

Column 17,  
Line 54, delete "a" and insert -- an acidic organic -- between the words "treating" and "liquid".  
Line 55, insert -- acidic organic -- between the words "the" and "liquid".

Column 18,  
Line 2, delete "exchnaged" and insert -- exchanged --.  
Line 5, delete "absorb" and insert -- adsorb --  
Line 6, add -- acidic organic -- between the words "treated" and "liquid".

Signed and Sealed this

Third Day of September, 2002

Attest:

Attesting Officer

JAMES E. ROGAN  
Director of the United States Patent and Trademark Office